(12) United States Patent
Yang et al.

(10) Patent No.: US 11,672,513 B2
(45) Date of Patent: Jun. 13, 2023

(54) METHOD, APPARATUS, AND SYSTEM FOR ADJUSTING BRIGHTNESS OF ULTRASOUND IMAGE BY USING PRESTORED GRADATION DATA AND IMAGES

(71) Applicant: SAMSUNG MEDISON CO., LTD., Gangwon-do (KR)

(72) Inventors: Sun-Mo Yang, Gangwon-do (KR); Chul-An Kim, Gangwon-do (KR); Jae-Moon Jo, Seongnam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 236 days.

(21) Appl. No.: 16/599,815

(22) Filed: Oct. 11, 2019

(65) Prior Publication Data

US 2020/0037999 A1  Feb. 6, 2020

Related U.S. Application Data

(63) Continuation of application No. 14/493,063, filed on Sep. 22, 2014, now Pat. No. 10,517,573.

(30) Foreign Application Priority Data

Apr. 1, 2014  (KR) .................... 10-2014-0038749

(51) Int. Cl.
*A61B 8/00* (2006.01)
*G01S 7/52* (2006.01)
*A61B 8/08* (2006.01)

(52) U.S. Cl.
CPC ............... *A61B 8/58* (2013.01); *A61B 8/463* (2013.01); *A61B 8/467* (2013.01); *A61B 8/52* (2013.01);

(Continued)

(58) Field of Classification Search
CPC .......... A61B 8/58; A61B 8/463; A61B 8/467; A61B 8/52; A61B 8/00; A61B 8/08;
(Continued)

(56) References Cited

U.S. PATENT DOCUMENTS 5,482,045 A  1/1996 Rust et al.
6,050,942 A  4/2000 Rust et al.
(Continued)

FOREIGN PATENT DOCUMENTS

CN  103654860 A  3/2014
EP  1793343 A1  6/2007
(Continued)

OTHER PUBLICATIONS

Chinese Office Action dated Nov. 1, 2019 issued in Chinese Patent Application No. 201410680165.8 (with English translation).

(Continued)

*Primary Examiner* — Carolyn A Pehlke
(74) *Attorney, Agent, or Firm* — Morgan, Lewis & Bockius LLP

(57) ABSTRACT

Provided is a method of adjusting brightness of an ultrasound image including: generating at least one first image representing a region of interest (ROI) by using echo signals corresponding to ultrasound waves irradiated toward the ROI; adjusting brightness of the at least one first image based on an external signal for selecting at least one selected from a plurality of prestored gradation data and a plurality of prestored image data; and generating a second image representing the ROI based on the adjusted brightness.

9 Claims, 9 Drawing Sheets

(52) U.S. Cl.
CPC ...... *G01S 7/52033* (2013.01); *G01S 7/52084* (2013.01); *G01S 7/52063* (2013.01); *G01S 7/52074* (2013.01)

(58) Field of Classification Search
CPC ............. G01S 7/52033; G01S 7/52084; G01S 7/52063; G01S 7/52074
See application file for complete search history.

(56) References Cited

U.S. PATENT DOCUMENTS

| | | | |
|---|---|---|---|
| 6,468,212 B1* | 10/2002 | Scott ...................... | A61B 8/463 600/440 |
| 6,951,543 B2* | 10/2005 | Roundhill ........... | G01S 7/52074 600/443 |
| 7,324,673 B1 | 1/2008 | Yamanaka et al. | |
| 7,833,159 B2 | 11/2010 | Ahn et al. | |
| 7,956,906 B2 | 6/2011 | Nojima | |
| 8,016,759 B2 | 9/2011 | Lee et al. | |
| 9,320,490 B2 | 4/2016 | Kim et al. | |
| 2004/0019276 A1 | 1/2004 | Kim et al. | |
| 2004/0151358 A1 | 8/2004 | Yanagita et al. | |
| 2007/0081711 A1 | 4/2007 | Kim et al. | |
| 2007/0225930 A1 | 9/2007 | Kwun et al. | |
| 2007/0236492 A1 | 10/2007 | Ahn et al. | |
| 2008/0139932 A1 | 6/2008 | Lee et al. | |
| 2008/0242988 A1 | 10/2008 | Yoshida et al. | |
| 2009/0216123 A1 | 8/2009 | Matsumura et al. | |
| 2010/0069755 A1 | 3/2010 | Nishimura et al. | |
| 2010/0217126 A1* | 8/2010 | Yawata ................. | A61B 8/14 600/443 |
| 2011/0276283 A1 | 11/2011 | Lee et al. | |
| 2012/0232393 A1 | 9/2012 | Lee et al. | |
| 2013/0064036 A1 | 3/2013 | Lee et al. | |
| 2013/0090558 A1* | 4/2013 | Jo ......................... | A61B 8/465 600/437 |
| 2013/0144169 A1 | 6/2013 | Lee et al. | |
| 2014/0088428 A1 | 3/2014 | Yang et al. | |
| 2015/0153990 A1* | 6/2015 | Rust ...................... | G16H 30/40 345/2.2 |
| 2015/0359516 A1 | 12/2015 | Yang et al. | |

FOREIGN PATENT DOCUMENTS

| | | |
|---|---|---|
| EP | 1929952 A1 | 6/2008 |
| EP | 2702946 A1 | 3/2014 |
| EP | 2710960 A1 | 3/2014 |
| JP | 2007-098142 A | 4/2007 |
| JP | 2007-144181 A | 6/2007 |
| JP | 2009-178277 A | 8/2009 |
| JP | 2011-120707 A | 6/2011 |
| JP | 2012-195968 A | 10/2012 |
| KR | 10-0748858 B1 | 8/2007 |
| KR | 10-2008-0051917 A | 6/2008 |
| KR | 10-0989580 B1 | 10/2010 |
| KR | 10-2012-0056323 A | 6/2012 |

OTHER PUBLICATIONS

Chinese Office Action dated Jul. 2, 2019 issued in Chinese Patent Application No. 201410680165.8 (with English translation).
U.S. Notice of Allowance dated Jul. 9, 2019 issued in U.S. Appl. No. 14/493,063.
Chinese Office Action dated Jan. 28, 2019 issued in Chinese Patent Application No. 201410680165.8 (with English translation).
U.S. Final Office Action dated Apr. 24, 2019 issued in U.S. Appl. No. 14/493,063.
U.S. Non-Final Office Action dated Dec. 3, 2018 issued in U.S. Appl. No. 14/493,063.
The Scientist and Engineer's Guide to Digital Signal Processing, CH 24, copyright 1997-1998 by Steven W. Smith, 1998.
U.S. Non-Final Office Action dated Jul. 21, 2017 issued in U.S. Appl. No. 14/493,063.
U.S. Final Office Action dated Dec. 8, 2016 issued in U.S. Appl. No. 14/493,063.
U.S. Non-Final Office Action dated May 20, 2016 issued in U.S. Appl. No. 14/493,063.
Extended European Search Report dated Aug. 3, 2015 issued in European Patent Application No. 14177966.0.
Korean Notice of Allowance dated Jan. 29, 2021 issued in Korean Patent Application No. 10-2014-0038749 (with English translation).

* cited by examiner

METHOD, APPARATUS, AND SYSTEM FOR ADJUSTING BRIGHTNESS OF ULTRASOUND IMAGE BY USING PRESTORED GRADATION DATA AND IMAGES

RELATED APPLICATIONS

This application is a continuation patent application of U.S. patent application Ser. No. 14/493,063, filed on Sep. 22, 2014, which claims the benefit of Korean Patent Application No. 10-2014-0038749, filed on Apr. 1, 2014, in the Korean Intellectual Property Office, the disclosures of which are incorporated herein in their entireties by reference.

BACKGROUND

1. Field

One or more embodiments of the present invention relate to a method, apparatus, and system for adjusting brightness of an ultrasound image by using prestored gradation data and images.

2. Description of the Related Art

An ultrasound system is an important diagnostic system because it has a wide variety of applications. In particular, the ultrasound system has been widely used in the medical industry due to it being a non-invasive and non-destructive way to investigate an object. Recently, high performance ultrasound systems are being used to generate two-dimensional (2D) or three-dimensional (3D) images showing the internal structures of an object.

In order to transmit or receive an ultrasound signal, an ultrasound system generally includes a probe with a wide-band transducer. When the transducer is electrically stimulated, it produces an ultrasound signal and transmits the ultrasound signal to a human body. The ultrasound signal transmitted into the human body is reflected from a boundary between tissues inside the human body and returned to the transducer. The returned ultrasound echo signal is then converted into an electrical signal, and ultrasound image data for obtaining an image of tissue is generated by amplifying and signal-processing the electrical signal.

SUMMARY

One or more embodiments of the present invention include a method, an apparatus, and a system for adjusting brightness of an ultrasound image by using prestored gradation data and image data.

One or more embodiments of the present invention include a non-transitory computer-readable recording medium having recorded thereon a program for executing the method on a computer.

Additional aspects will be set forth in part in the description which follows and, in part, will be apparent from the description, or may be learned by practice of the presented embodiments.

According to one or more embodiments of the present invention, a method of adjusting brightness of an ultrasound image includes: generating at least one first image representing a region of interest (ROI) by using echo signals corresponding to ultrasound waves irradiated toward the ROI; adjusting brightness of the at least one first image based on an external signal for selecting at least one selected from a plurality of prestored gradation data and a plurality of prestored image data; and generating a second image representing the ROI based on the adjusted brightness.

According to one or more embodiments of the present invention, a non-transitory computer-readable recording medium has recorded thereon a program for executing the above-described method on a computer.

According to one or more embodiments of the present invention, an apparatus for adjusting brightness of an ultrasound image includes: an image generating unit for generating at least one first image representing an ROI by using echo signals corresponding to ultrasound waves irradiated toward the ROI; a storage unit for storing a plurality of gradation data or a plurality of image data; and a brightness adjusting unit for adjusting brightness of the at least one first image based on an external signal for selecting at least one selected from the plurality of gradation data and the plurality of image data, wherein the image generating unit generates a second image representing the ROI based on the adjusted brightness.

According to one or more embodiments of the present invention, an ultrasound diagnostic system includes: a probe that irradiates ultrasound waves toward an ROI of an object and receives echo signals corresponding to the ultrasound waves; and an image generating apparatus that generates at least one first image representing the ROI by using the echo signals, adjusts brightness of the at least one first image based on an external signal for selecting at least one selected from a plurality of prestored gradation data and a plurality of prestored image data, and generates a second image representing the ROI based on the adjusted brightness.

As described above, a method, an apparatus, and a system for adjusting brightness of an ultrasound image according to embodiments of the present invention are adapted to adjust brightness of a plurality of ultrasound images in real-time or later by using prestored gradation data and image data, thereby eliminating a user's inconvenience of having to adjust brightness of one image and then selecting another image and adjusting brightness of the other image. Furthermore, it is possible to adjust brightnesses of different regions in each of a plurality of images obtained by copying one image, thereby facilitating comparison and analysis of the plurality of images.

The method, apparatus, and system for adjusting brightness of an ultrasound image are also adapted to prestore preset data (including gradation data and image data) and update (i.e., add or delete) the preset data according to user selection, thereby allowing a user to easily select an optimized degree of brightness for each object.

Furthermore, it is possible to arbitrarily increase or reduce the number of objects (i.e., brightness adjustment tools) for adjusting brightness of an ultrasound image or freely change a location where the object is displayed, thereby increasing user convenience.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Embodiments of the invention will be described more fully hereinafter with reference to the accompanying drawings, in which illustrative embodiments of the invention are shown. It should be understood that the exemplary embodiments described herein should be considered in a descriptive sense only and not for purposes of limitation. All technical concepts that can easily be inferred from the detailed description and embodiments of the present invention by one of ordinary skill in the art should be construed as being included in the scope of the present invention. Expressions such as "at least one of," when preceding a list of elements, modify the entire list of elements and do not modify the individual elements of the list.

Figure 1:
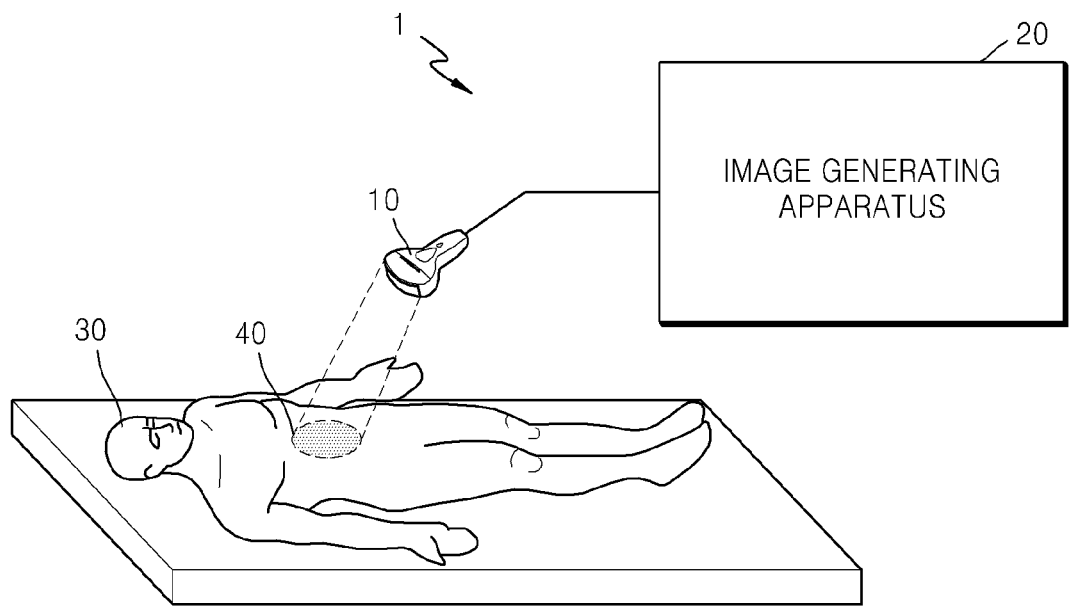
FIG. 1 is a diagram illustrating a configuration of an ultrasound diagnostic system according to an exemplary embodiment of the present invention.

FIG. 1 is a diagram illustrating a configuration of an ultrasound diagnostic system 1 according to an exemplary embodiment of the present invention.

Referring to FIG. 1, the ultrasound diagnostic system 1 includes a probe 10 and an image generating apparatus 20. Although the ultrasound diagnostic system 1 only includes components related to the present embodiment, it will be understood by one of ordinary skill in the art that the ultrasound diagnostic system 1 may further include other common components in addition to those illustrated in FIG. 1.

The probe 10 irradiates ultrasound waves toward a region of interest (ROI) 40 of an object 30 and receives echo signals corresponding to the ultrasound waves. The probe 10 also transmits the echo signals to an image generating unit 220 in the image generating apparatus 20.

In detail, when transducers (not shown) in the probe 10 transmit ultrasound waves to a specific portion inside the object 30, the ultrasound waves are partially reflected from layers between different tissues. In particular, the ultrasound waves may be reflected from an area of the object 30 where there is a change in density, e.g., from blood cells within blood plasma or small structures within organs. The reflected ultrasound waves vibrate the transducers, and the transducers output electrical pulses corresponding to the vibrations. The probe 10 transmits the electrical pulses to the image generating unit 220.

Here, the object 39 means a subject, e.g., a patient, of which an image is generated, but is not limited thereto. The ROI 40 means a predetermined region in the object 30, e.g., a lesion tissue, but is not limited thereto.

The image generating apparatus 20 generates at least one first image representing the ROI 40 by using echo signals. In this case, the first image means an ultrasound image representing the ROI 40. The image generating apparatus 20 also adjusts brightness of the first image based on an external signal for selecting at least one selected from a plurality of prestored gradation data and a plurality of prestored image data and generates a second image representing an ROI based on the adjusted brightness. The image data means data corresponding to information contained in an image, and the information includes information about brightness of the image. Furthermore, the second image means an ultrasound image representing the ROI 40. The external signal means a signal input from outside the image generating apparatus 20. For example, the external signal may be input by a user through an input device (not shown) including input elements such as a mouse, a keyboard, and a touch display and software modules for driving the input elements. The image generating apparatus 20 display the first and second images.

The operation of an image generating apparatus 20 will now be described in more detail with reference to FIGS. 2 through 10.

Figure 2:
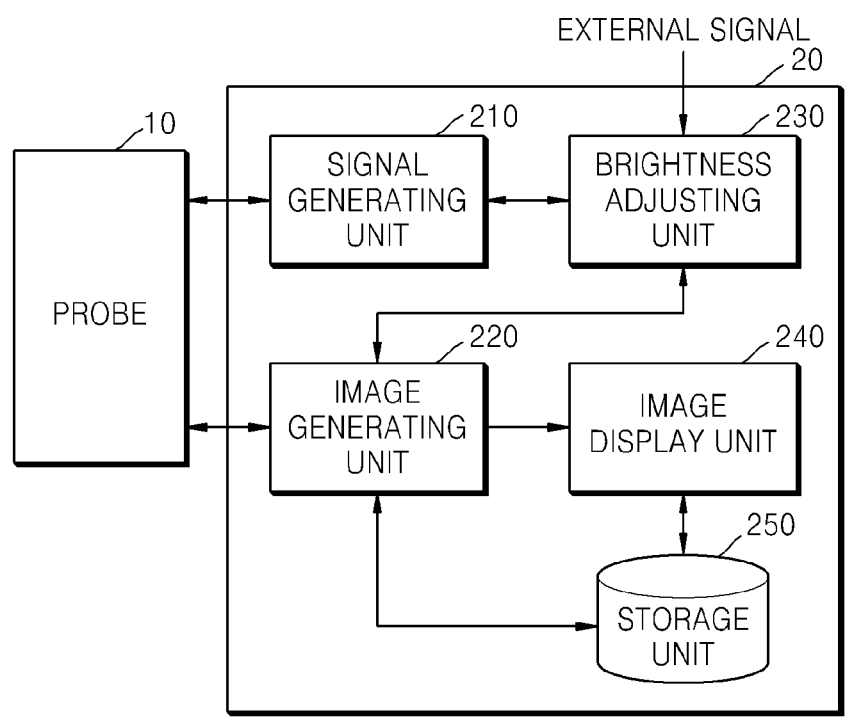
FIG. 2 is a block diagram of a configuration of an image generating apparatus according to an exemplary embodiment of the present invention.

FIG. 2 is a block diagram of a configuration of the image generating apparatus 20 according to an exemplary embodiment of the present invention.

Referring to FIG. 2, the image generating apparatus 20 according to the present embodiment includes a signal generating unit 210, a brightness adjusting unit 230, an image generating unit 220, an image display unit 240, and a storage unit 250. Although the image generating apparatus 20 of FIG. 2 only includes components related to the present embodiment, it will be understood by those of ordinary skill in the art that the image generating apparatus 20 may further include common components other than those illustrated in FIG. 2.

It will also be obvious to those of ordinary skill in the art that the image display unit 240 may be formed as an independent image display device. In other words, the image display unit 240 may include all output devices such as a display panel, a monitor, etc., mounted in the ultrasound diagnostic system 1, and software modules for driving the output devices.

Furthermore, the signal generating unit 210, the brightness adjusting unit 230, and the image generating unit 220 in the image generating apparatus 20 may correspond to one or a plurality of processors. The processor(s) may be implemented as an array of multiple logic gates, or a combination of a universal microprocessor and a memory for storing a program that can be executed in the universal microprocessor. Furthermore, it will be understood by those of ordinary skill in the art that the processor(s) may be formed using a different type of hardware.

The signal generating unit 210 generates ultrasound signals to be transmitted by the probe 10 to the ROI 40. In detail, the signal generating unit 210 generates electrical signals corresponding to ultrasound waves to be irradiated by the probe 10 in consideration of locations of the transducers in the probe 10 and a point at which the transducers focus ultrasound waves. In this case, the signal generating unit 210 may generate a plurality of electrical signals by sequentially and iteratively producing electrical signals according to a position or size of the ROI 40. The signal generating unit 210 transmits the generated electrical signals to the probe 10 which in turn irradiates ultrasound waves corresponding to the electrical signals toward the ROI 40.

The image generating unit 220 generates at least one first image representing the ROI 40 by using echo signals corresponding to the ultrasound waves. In this case, the first image means an ultrasound image showing the ROI 40. For example, the first image may be a brightness (B) mode image, a motion (M) mode image, a Doppler mode image, a color (C) mode image, or an elasticity mode image. The first image may be a two-dimensional (2D) or three-dimensional (3D) image.

In detail, the image generating unit 220 produces a digital signal by performing analog-to-digital conversion on the echo signals (i.e., electrical pulses) received from the probe 10. The image generating unit 220 also creates a focused reception signal by performing reception beamforming on the digital signal, and ultrasound data by using the focused reception signal. The ultrasound data may include a radio frequency (RF) signal, but is not limited thereto.

The image generating unit 220 also generates a first image showing the ROI 40 by using the ultrasound data. In this case, the first image showing the ROI 40 may represent shapes and sizes of tissues contained in the ROI 40.

The image display unit 240 displays a first image generated by the image generating unit 220. Although the image display unit 240 is incorporated into the image generating apparatus 20, it may be separate from the image generating apparatus 20. In detail, the image display unit 240 includes all output devices such as a display panel, a monitor, etc., and software modules for driving the output devices.

An example of a first image generated by the image generating unit 220 will now be described in greater detail with reference to FIGS. 3 and 4.

Figure 3:
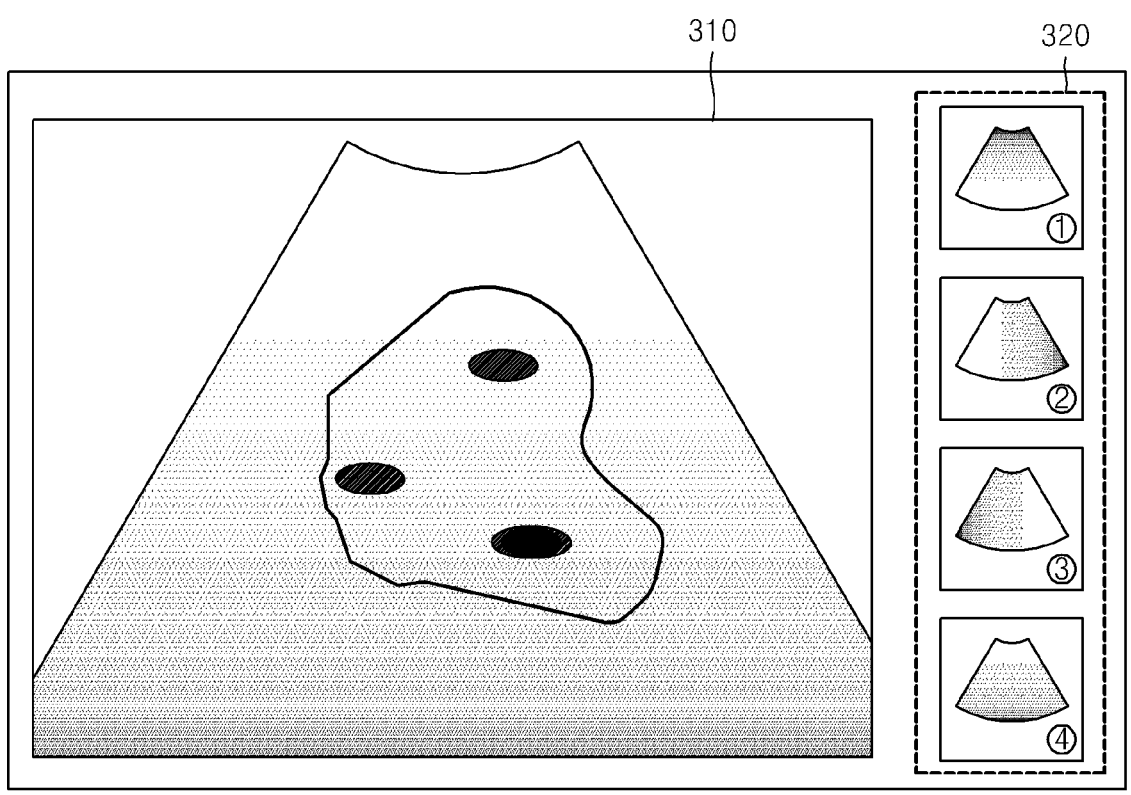
FIG. 3 is a diagram for explaining a first image according to an exemplary embodiment of the present invention.

FIG. 3 is a diagram for explaining a first image 310 according to an exemplary embodiment of the present invention.

FIG. 3 illustrates an example of the first image 310 that is generated by the image generating unit 220 and displayed on the image display unit 240. Since ultrasound waves are attenuated as the ultrasound waves penetrate deeper into tissue, an echo signal reflected from a region located close to a surface of the probe 10 has a different magnitude or phase from that reflected from a region located away from the surface of the probe 10. Thus, since a portion in the first image 310 representing the region located away from the surface of the probe 10 appears dark, the user may have difficulty in analyzing the first image 310.

In the image generating apparatus 20, the brightness adjusting unit 230 adjusts brightness of the first image 310 by using prestored gradation data or image data. The image generating unit 220 generates a second image based on the adjusted brightness, and the image display unit 240 displays the second image. Thus, the user is able to adjust brightness of an image of a desired region to a desired level.

In this case, the brightness adjusting unit 230 may adjust the brightness of a first image based on an external signal for selecting at least one selected from a plurality of gradation data 320 and a plurality of image data. A method of adjusting brightness of a first image, which is performed by the brightness adjusting unit 230, will be described in detail below with reference to FIGS. 5 through 9.

Figure 4:
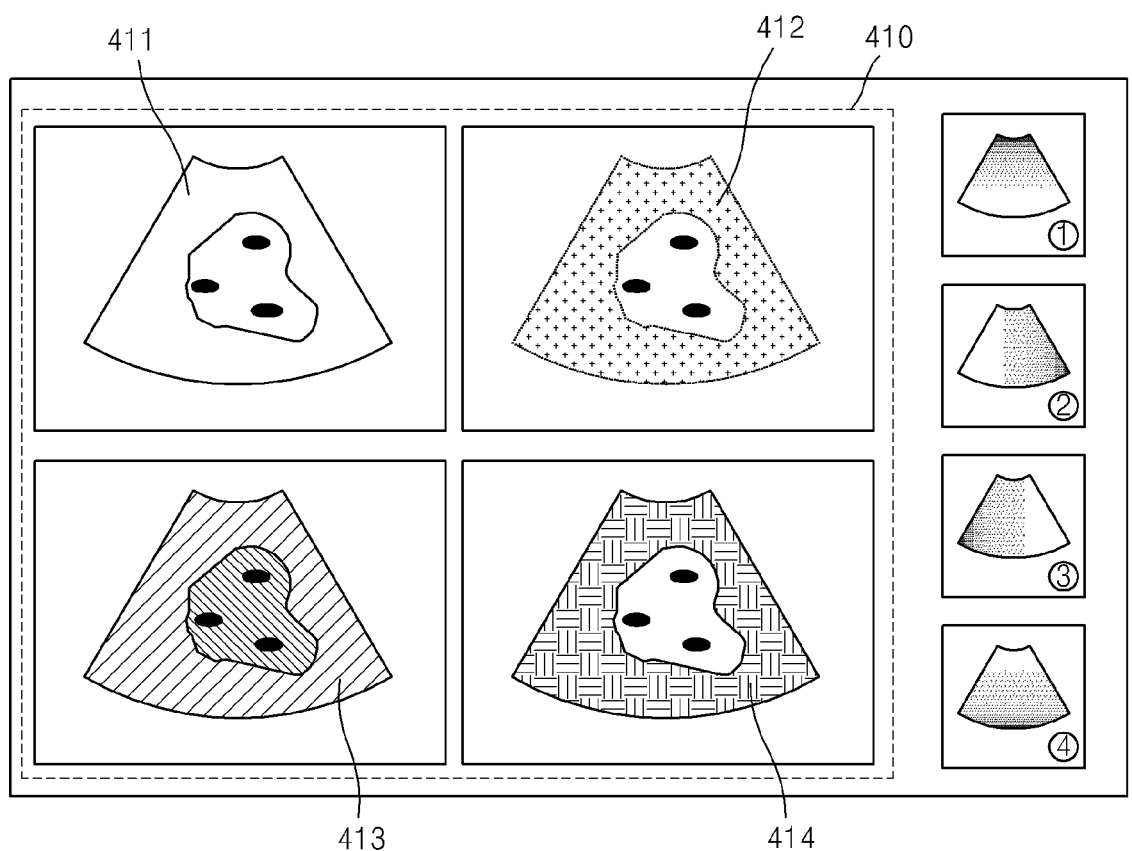
FIG. 4 is a diagram for explaining a first image according to another exemplary embodiment of the present invention.

FIG. 4 is a diagram for explaining a first image 410 according to another exemplary embodiment of the present invention.

FIG. 4 illustrates an example where a plurality of first images 411 through 414 generated by the image generating unit 220 are displayed on the image display unit 240. In this case, the plurality of first images 411 through 414 may be a plurality of copies of the same image or a plurality of different images. For example, although the probe 10 repeatedly irradiates ultrasound waves toward the same ROI (40 in FIG. 1), received echo signals may have different magnitudes or phases from one other. Thus, the first images 411 through 414 may be the same as or different from one another.

As described above, the image generating apparatus 20 may display the plurality of first images 411 through 413, thereby allowing a user to adjust brightness of each of the first images 411 through 414 as well as different regions in each of the first images 411 through 414.

Referring back to FIG. 2, the brightness adjusting unit 230 adjusts brightness of a first image based on the received external signal. In this case, the external signal means a signal that is used for selecting at least one selected from a plurality of prestored gradation data and a plurality of prestored image data and is input from outside the image generating apparatus 20. The image data is data corresponding to information contained in an image, and the information includes information representing brightness of the image. In detail, the brightness adjusting unit 230 may adjust brightness of the whole or a portion of the first image corresponding to gradation data or image data selected based on the external signal. For example, the brightness adjusting unit 230 may adjust brightness of the first image by changing a Time Gain Compensation (TGC) value or a Lateral Gain Compensation (LGC) value of the first image so that the TGC or LGC value of the first image is equal to brightness of an image contained in the selected gradation data or image data.

The storage unit 250 stores a plurality of gradation data and a plurality of image data. Here, the gradation data is data corresponding to gradations represented in images previously generated by the image generating unit 220. The image data is data representing all types of information contained in the previously generated images, and the all types of information include information representing brightness of the images.

As described above, as ultrasound waves irradiated by the probe 10 penetrate deeper, the ultrasound waves are attenuated, and the degree of attenuation varies depending on a location of the ROI 40 and various conditions such as types of tissues contained in the ROI 40. Thus, gradations represented in images generated by the image generating unit 220 may vary from one image to another.

The storage unit 250 stores data corresponding to gradations that are respectively represented in previously generated images as preset data. The storage unit 250 reads at least one of the stored data based on an external signal. Thus, the brightness adjusting unit 230 may adjust brightness of a first image so that it corresponds to one gradation or brightness of an image in the preset data, thereby eliminating the need for a user to manually adjust the brightness of the first image whenever necessary.

The storage unit 250 may also store data corresponding to brightness of the first image as preset data in the form of an image or gradation. In detail, the storage unit 250 may add data corresponding to the brightness of the first image to the preset data as gradation data and store the resulting data. The storage unit 250 may also add data (including data corresponding to the brightness of the first image) corresponding to all types of information contained in the first image to the preset data as image data and store the resulting data. In other words, since it is possible to update (i.e., add or delete) the preset data stored in the storage unit 250, desired data may be stored for each user. The brightness adjusting unit 230 may adjust brightness of an image by using the updated preset data.

The image generating unit 220 generates a second image representing the ROI 40 based on brightness obtained by the brightness adjusting unit 230. In other words, the first and second images generated by the image generating unit 220 may represent the same ROI 40 but exhibit different brightnesses.

For example, the image generating unit 220 amplifies an echo signal received from the probe 10 and adjusts a gain of the amplified echo signal. In detail, the image generating unit 220 adjusts a gain of an echo signal based on a TGC or LGC value received from the brightness adjusting unit 230 and regenerate ultrasound data. The image generating unit 220 also generates a second image by using the regenerated ultrasound data.

The image display unit 240 displays the first and second images generated by the image generating unit 220. The image display unit 240 may display the first and second images simultaneously on the same screen, or display them sequentially.

The image display unit 240 also reads a plurality of gradation data and a plurality of image data for adjusting brightness of the first image from the storage unit 250 and displays the plurality of gradation data and the plurality of image data on a screen. Thus, the user may select the degree to which the brightness of the first image will be changed by selecting one of the plurality of gradation data and the plurality of image data displayed on the screen.

Furthermore, the image display unit 240 may display at least one object for adjusting brightness of the first image. In this case, an object may represent each of the plurality of gradation data and the plurality of image data stored in the storage unit 250, or correspond to a digital TGC or LGC module. The image display unit 240 may display the first image and an object on the same screen in an overlapping manner, or change a region where the object is displayed independently from the first image based on an external signal. In addition, the image display unit 240 may display the object by changing transparency thereof based on an external signal, or display the object only when an external signal for changing a location of the object is received.

A method of adjusting brightness of a first image will now be described in more detail with reference to FIGS. 5 through 9.

Figure 5A:
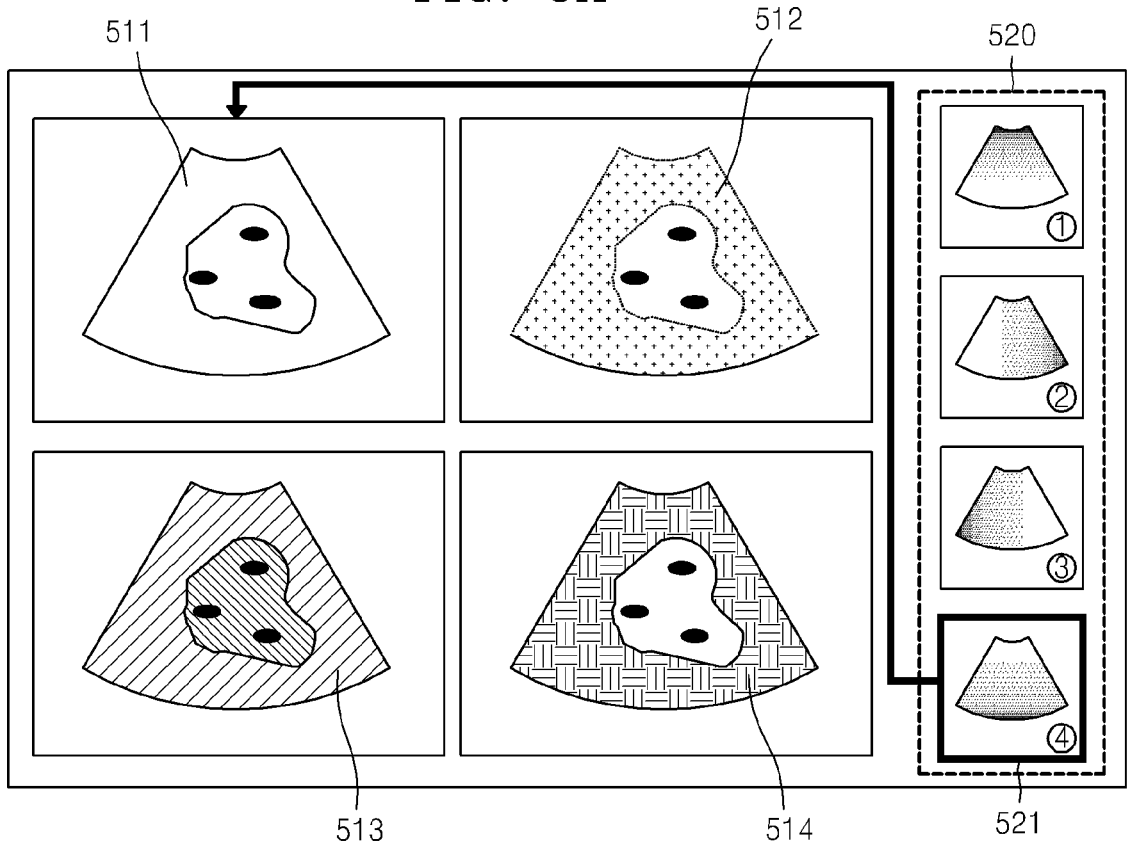
FIGS. 5A and 5B are diagrams for explaining adjustment of brightness of a first image according to an exemplary embodiment of the present invention.
Figure 5B:
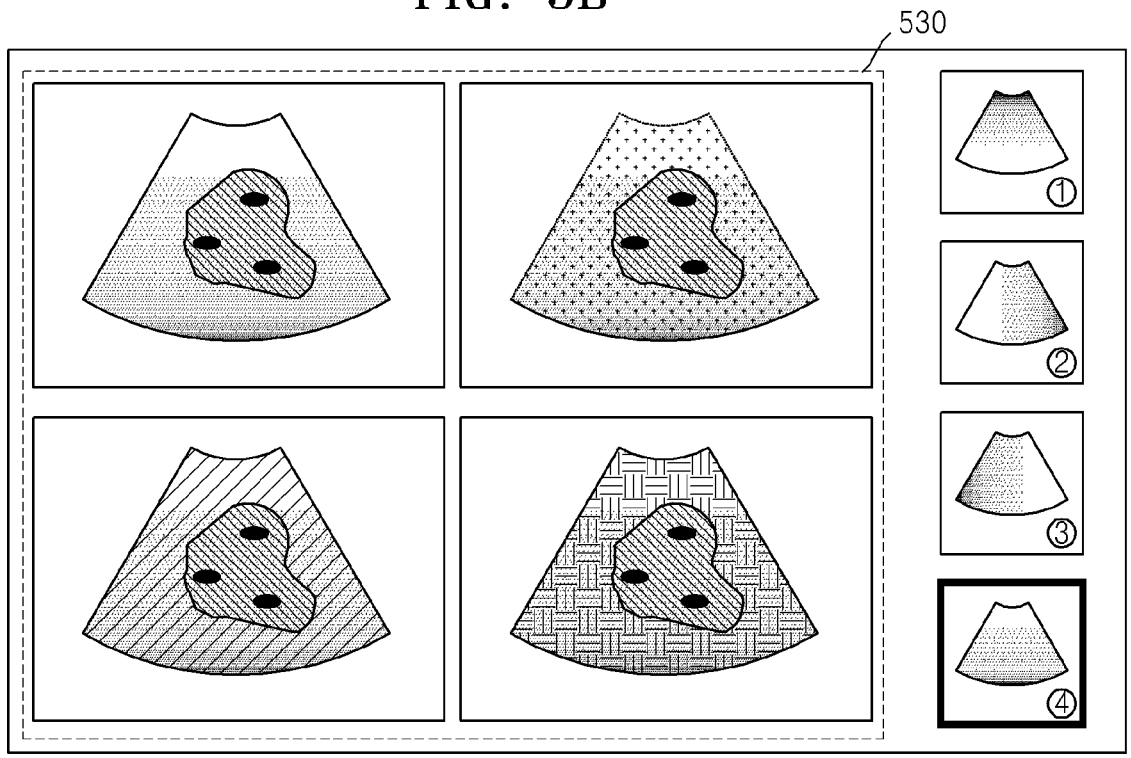

FIGS. 5A and 5B are diagrams for explaining adjustment of brightness of a plurality of first images 511 through 514 according to an exemplary embodiment of the present invention. In particular, FIG. 5A illustrates an example where the image display unit (240 in FIG. 2) displays the plurality of first images 511 through 514 and a plurality of objects 520 for adjusting brightness of the plurality of first images 511 through 514.

The objects 520 represent a plurality of gradation data and a plurality of image data stored in the storage unit 250. For example, the objects 520 may include an object representing a gradation that becomes gradually darker from a lower end of an image to an upper end thereof, an object representing a gradation that becomes gradually darker from the left side of an image toward the right side thereof, an object representing a gradation that becomes gradually darker from the right side of an image toward the left side thereof, and an object 521 representing a gradation that becomes gradually darker from an upper end of an image to a lower end thereof. Each of the objects 520 may show a shape of tissue in an ROI of an object, or only indicate brightness of an image without showing the shape of tissue. Although FIG. 5A shows that the number of the objects 520 is four (4) for convenience of explanation, the number of the objects 520 may vary depending on the number of data stored in the storage unit 250 and the number of regions of which brightness is adjusted.

Based on an external signal for selecting one of a plurality of gradation data and a plurality of image data, the brightness adjusting unit 230 adjusts brightness of the first image to a level corresponding to the selected data. Here, the external signal is a signal for selecting one of the objects 520 corresponding to the plurality of data, respectively.

For example, if an external signal for selecting the object 521 representing the gradation that becomes gradually darker from the upper end of the image to the lower end thereof is received, the brightness adjusting unit 230 adjusts brightness of one or all of the first images 511 through 514 to a brightness level corresponding to the selected object 521. In other words, the brightness adjusting unit 230 may adjust brightnesses of the first images 511 through 514 so that they are equal to or different from one another.

FIG. 5B illustrates an example where the image display unit 240 displays a plurality of second images 530. The second images 530 may be obtained by adjusting the brightness of the first images 511 through 514 shown in FIG. 5A to a brightness level corresponding to the selected object 521.

Referring to FIG. 5B, the brightness of the second images 530 is adjusted to have a gradation that becomes gradually darker from an upper end of an image towards a lower end thereof. Although FIG. 5B shows that the brightness of all the second images 530 is adjusted to have the same level, for convenience of explanation, only brightness of one of the second images 530 may be adjusted to a level corresponding to the selected object 521. In other words, based on an external signal for selecting one of the first images 511 through 514 shown in FIG. 5A, the brightness adjusting unit 230 may adjust only brightness of the selected first image 511 to a level corresponding to the selected object 521.

Figure 6:
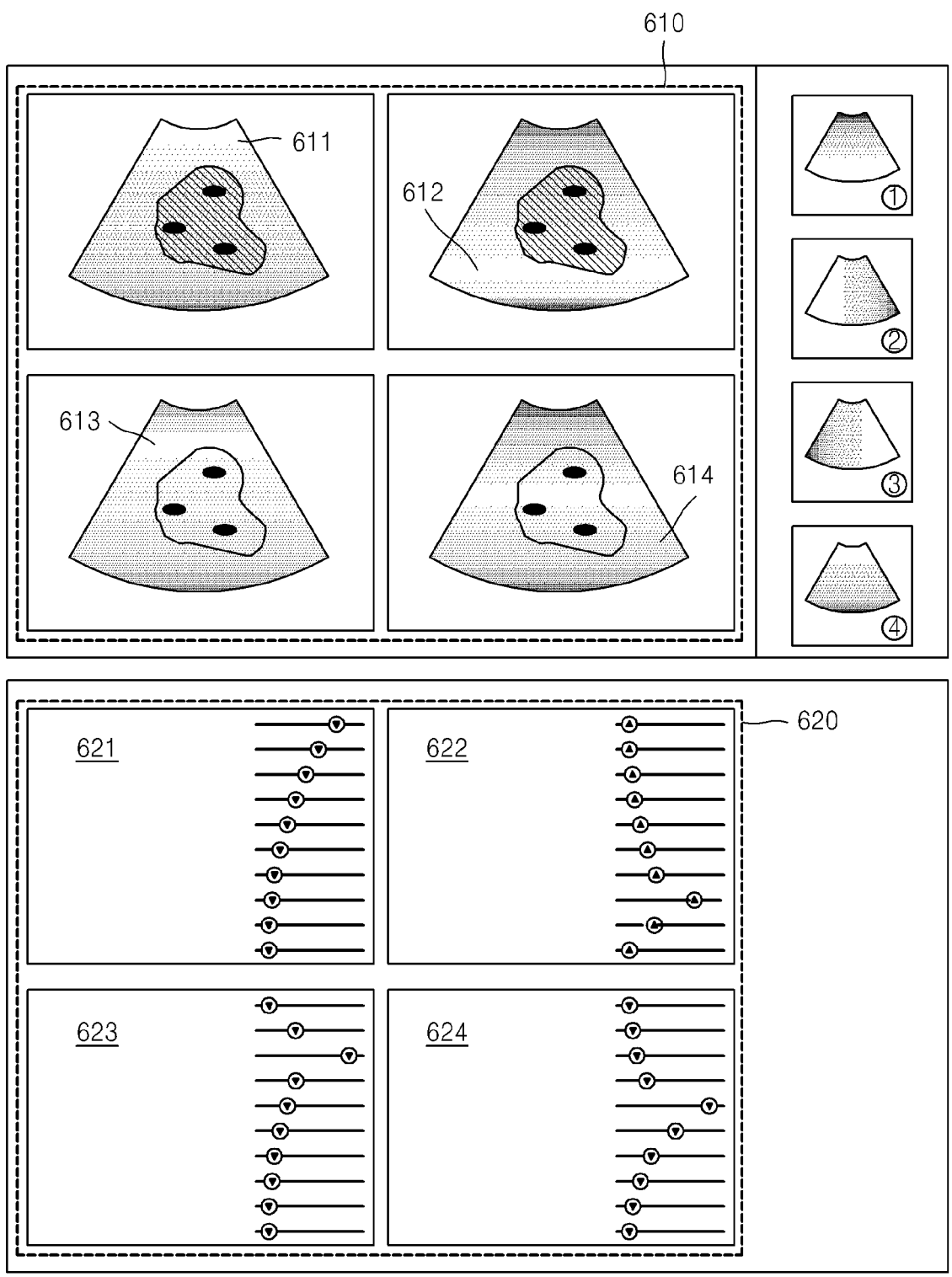
FIG. 6 is a diagram for explaining adjustment of brightness of a first image according to another exemplary embodiment of the present invention.
Figure 7:
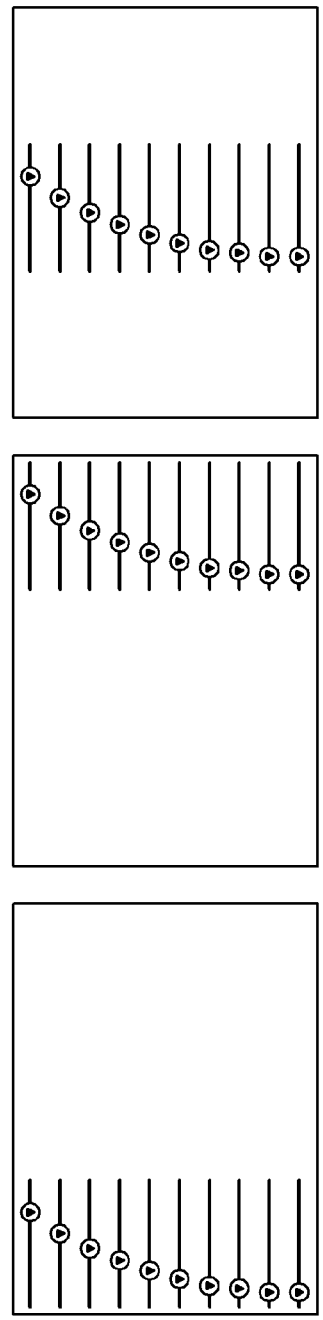
FIGS. 7A through 7C are diagrams for explaining examples where an image display unit changes a region where an object is displayed according to an exemplary embodiment of the present invention.

FIG. 6 is a diagram for explaining adjustment of brightness of first images according to another exemplary embodiment of the present invention. Referring to FIG. 6, the image display unit (240 in FIG. 2) displays second images 610 (or 611 through 614) and objects 620 (or 621 through 624) for adjusting brightness of the first images on separate regions, respectively. In this case, each of the objects 621 through 624 corresponds to a digital TGC or LGC module. Although FIG. 6 shows the second images 611 through 614 for convenience of explanation, the image display unit 240 may display the first images before displaying the second images 611 through 614.

The image display unit 240 displays the same number of the objects 621 through 624 as the first images. For example, if the number of the first images displayed on the image display unit 240 is 4, the image display unit 240 may display the four objects 621 through 624 corresponding to the first images, respectively. The brightness adjusting unit 230 may adjust brightness of the first images based on an external signal for changing a location of each of the objects 621 through 624.

In this case, each of the objects 621 through 624 includes icons for adjusting brightnesses of a plurality regions in each of the first images. For example, if each of the first images is partitioned into ten (10) regions, the image display unit 240 may display the objects 621 through 624, each including ten icons, so as to adjust brightness of each of the ten regions. Here, the number of ions (i.e., the number of regions in the first image) may be preset in the image generating apparatus (20 in FIG. 2) or be set by a user through an external signal.

The brightness adjusting unit 230 partitions each of the first images into a plurality of regions based on an external signal, and adjusts brightness of each of the plurality of regions in the first image. For example, if each of the objects 621 through 624 includes ten icons as shown in FIG. 6, the brightness adjusting unit 230 may divide the first image into ten regions, and adjust brightness of each of the ten regions respectively corresponding to the ten icons based on an external signal for moving at least one of the ten icons. The image generating unit 220 generates the second images 611 through 614, each having the ten regions of which brightness has been adjusted, and the image display unit 240 displays the second images 611 through 614.

For example, if an external signal for moving icons in the object 621 for making the first image darker towards the lower end is received, the image generating unit 220 may generate the second image 611 corresponding to positions of the icons, and the image display unit 240 may display the generated second image 611.

Furthermore, if an external signal for moving icons of the object 624 so that a central region of the first image is the brightest is received, the image generating unit 220 may generate the second image 614 corresponding to positions of the icons, and the image display unit 240 may display the generated second image 614.

As described above, the brightness adjusting unit 230 adjusts brightness of the first image by partitioning the first image into a plurality regions, the user may adjust brightness of only a region in the first image that the user desires to observe.

Although FIG. 6 illustrates an example where all the objects 621 through 624 are displayed on the right side of a screen, the image display unit 240 may change a region where the objects 621 through 624 are displayed. An example where the image display unit 240 changes a region where an object is displayed will now be described in detail with reference to FIG. 7.

FIGS. 7A through 7C are diagrams for explaining examples where the image display unit 240 changes a region where an object is displayed according to an exemplary embodiment of the present invention.

An object may be displayed based on an external signal for changing a region where the object is displayed. For example, as shown in FIG. 7A, the image display unit 240 may display an object on the left side of a screen based on an external signal for moving the object to the left side thereof. Furthermore, as shown in FIG. 7B, the image display unit 240 may display an object on the right side of a screen based on an external signal for moving the object to the right side thereof. In addition, as shown in FIG. 7C, the image display unit 240 may display an object at a central region of a screen based on an external signal for moving the object to the center thereof.

Although FIGS. 5 and 6 illustrate examples where the objects 520 or 621 through 624 are displayed separately from ultrasound images (i.e., the first or second images), the image display unit 240 may display an ultrasound image and an object on the same screen simultaneously.

Figure 8:
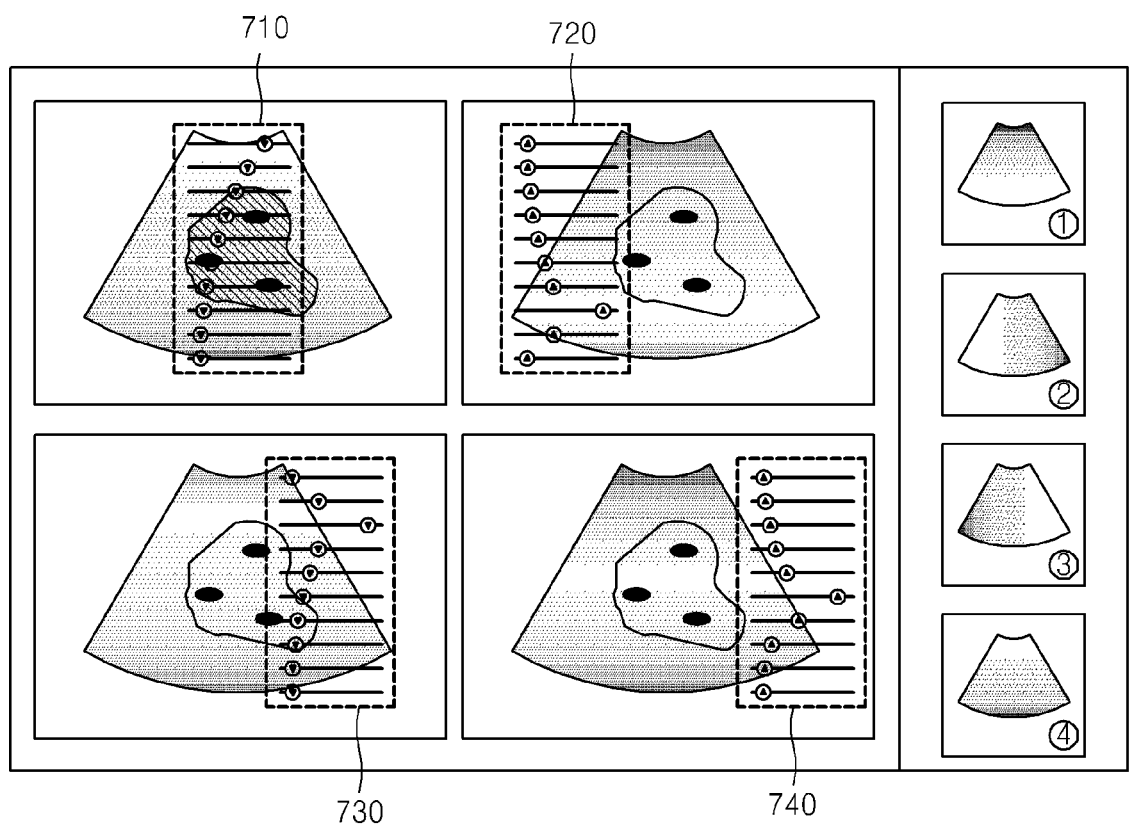
FIG. 8 is a diagram for explaining an example where an image display unit displays an ultrasound image (i.e., a first or second image) simultaneously with an object.

FIG. 8 is a diagram for explaining an example where the image display unit 240 displays ultrasound images (i.e., first or second images) and corresponding objects 710, 720, 730, and 740 simultaneously.

Referring to FIG. 8, second images and the objects 710, 720, 730, and 740 are displayed on the same screen simultaneously. While FIG. 8 shows the second images for convenience of explanation, the image display unit 240 may display first images before displaying the second images.

For example, the image display unit 240 may display the object 710 at a central portion of the second image, or the object 720 on the left side of the second image. Alternatively, the image display unit 240 may display the objects 730 and 740 on the right sides of the second images, respectively. In this case, the image display unit 240 may display the object 740 on the rightmost side of a screen and the object 730 at a position between the rightmost side and a central portion of the screen.

Figure 9A:
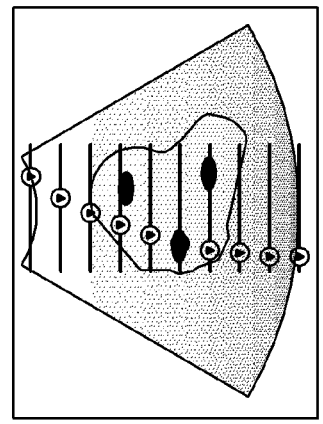
FIGS. 9A through 9C are diagrams for explaining another example where an image display unit displays an ultrasound image (i.e., a first or second image) simultaneously with an object.
Figure 9B:
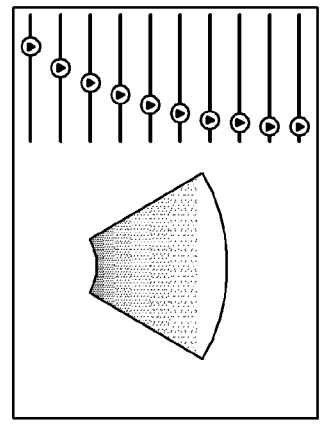
Figure 9C:
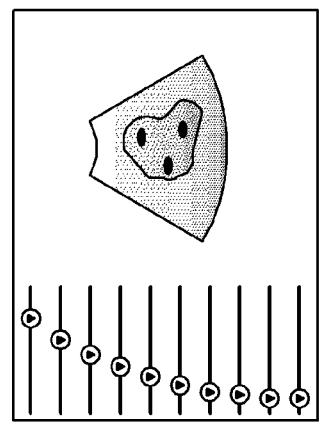

FIGS. 9A through 9C are diagrams for explaining another example where the image display unit 240 displays an ultrasound image (i.e., a first or second image) simultaneously with an object. Referring to FIGS. 9A through 9C, an ultrasound image and a corresponding object are displayed on the same screen simultaneously. While FIGS. 9A through 9C show second images for convenience of explanation, the image display unit 240 may display first images before displaying the second images.

Referring to FIGS. 9A and 9B, the image display unit 240 may display objects having sizes larger than those of the second images. Alternatively, referring to FIG. 9C, the image display unit 240 may display an object having the same size as the second image. In this case, the objects may be displayed at various positions without limitation, as described above with reference to FIG. 8.

Referring to FIGS. 5 through 9, objects are displayed opaquely. The image display unit 240 may display the objects opaquely so that the objects are separate and distinct from ultrasound images.

Furthermore, the image display unit 240 may display an object based on an external signal for changing transparency of the object. For example, the image display unit 240 may determine transparency of an object based on an external signal for setting the transparency of the object to a value between 0% and 100%, and display the object according to the determined transparency.

In addition, the image display unit 240 may display an object only when an external signal for changing a position of the object (i.e., for moving icons contained in the object) is received. Here, the external signal for changing the position of the object includes an external signal for moving a cursor position on a screen in order to move icons contained in the object or a touch signal input to a touch screen. The image display unit 240 may display the object only when the above external signal is received, and when the external signal is not received, may display only ultrasound images (i.e., first or second images).

Figure 10:
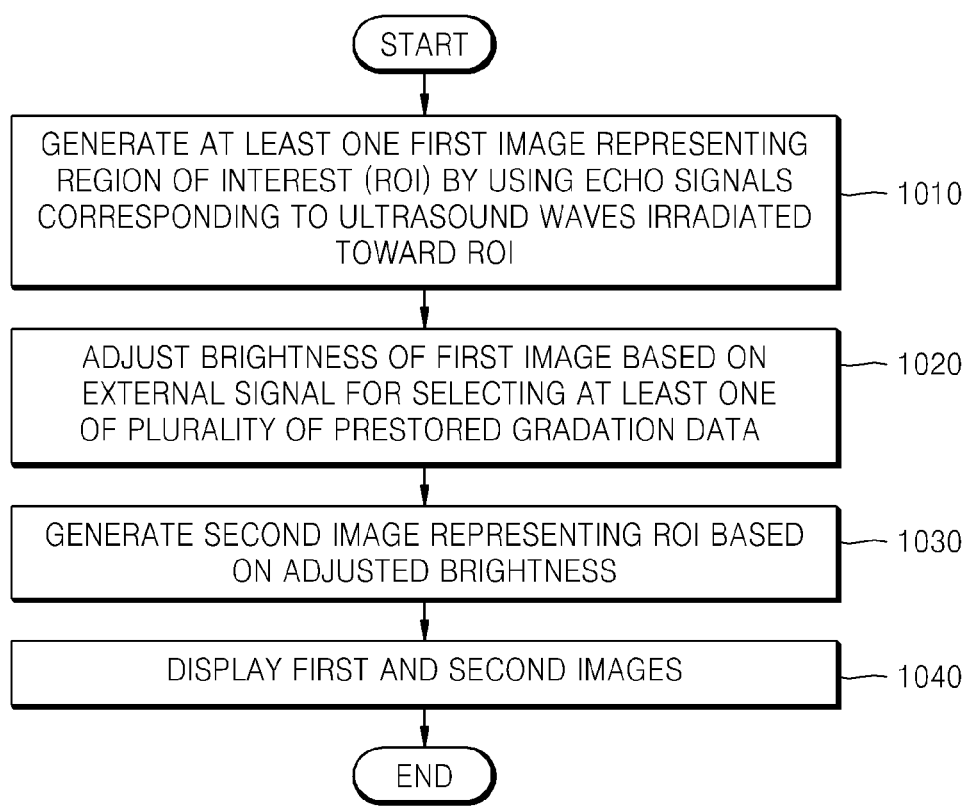
FIG. 10 is a flowchart of a method of adjusting brightness of an ultrasound image according to an exemplary embodiment of the present invention.

FIG. 10 is a flowchart of a method of adjusting brightness of an ultrasound image according to an exemplary embodiment of the present invention.

Referring to FIG. 10, the method of adjusting brightness of an ultrasound image according to the present embodiment includes operations performed sequentially by the ultrasound diagnostic system (1 in FIG. 1) or the image generating apparatus (20 in FIG. 2). Thus, even if omitted, the descriptions with respect to the ultrasound diagnostic system 1 or the ultrasound generating apparatus 20 shown in FIGS. 1 and 2 may be applied to the method illustrated in FIG. 10.

Referring to FIGS. 1, 2 and 10, the image generating unit 220 generates at least one first image representing the ROI 40 by using echo signals corresponding to ultrasound waves irradiated toward the ROI 40 (Operation 1010).

The brightness adjusting unit 230 adjusts brightness of the first image based on an external signal for selecting at least one of a plurality of prestored gradation data (Operation 1020).

The image generating unit 220 generates a second image representing the ROI 40 based on an adjusted brightness (Operation 1030).

The image display unit 240 displays the first and second images (Operation 1040).

The above method according to the embodiment of the present invention can be recorded in programs that can be executed on a computer and be implemented through general purpose digital computers which can run the programs using a computer-readable recording medium. Data structures described in the above method can also be recorded on a computer-readable medium in a variety of ways, with examples of the medium including recording media, such as magnetic storage media (e.g., read-only memory (ROM), random access memory (RAM), universal serial bus (USB), floppy disks, hard disks, etc.) and optical recording media (e.g., CD-ROMs or DVDs).

While one or more embodiments of the present invention have been described with reference to the figures, it will be understood by those of ordinary skill in the art that various changes in form and details may be made therein without departing from the spirit and scope of the present invention as defined by the following claims. Thus, the exemplary embodiments described herein should be considered in a descriptive sense only and not for purposes of limitation. The scope of the invention is defined not by the detailed description of the invention but by the appended claims, and all differences within the scope of the appended claims and their equivalents will be construed as being included in the present invention.

What is claimed is:

1. A method of adjusting brightness of an ultrasound image, the method comprising:
generating, by a processor, at least one first image representing a region of interest (ROI) by using echo signals corresponding to ultrasound waves irradiated toward the ROI;
displaying, by a screen, the at least one first image and a plurality of objects representing preset data of previously generated images, each of the plurality of objects showing a shape of a tissue in the ROI, wherein the plurality of objects respectively showing gradations of the ROI are displayed as image data that allows a degree of change in brightness of the gradations of the ROI to be recognized, and wherein the preset data includes a plurality of gradation data corresponding to the gradations of the previously generated images;
adjusting, by the processor, brightness of the at least one first image to generate at least one second image based on a first external signal for selecting a first object from the plurality of objects; and
displaying, by the screen, the at least one second image, wherein the gradations represented in the previously generated images vary from one image to another, wherein each of the plurality of objects includes icons for adjusting brightnesses of a plurality of regions in the at least one first image, and
wherein a number of the icons is the same as a number of the plurality of regions included in the at least one first image, and the brightnesses of the plurality of regions corresponding to the icons are adjusted.

2. The method of claim 1, further comprising storing data corresponding to the brightness of the at least one first image or the at least one second image as the gradation data.

3. The method of claim 1, wherein the at least one first image comprises a plurality of images representing the ROI, and
wherein in the generating of the at least one second image, brightnesses of the plurality of images are adjusted so that the brightnesses of the plurality of images are equal to one another based on the first external signal.

4. The method of claim 1, wherein the at least one first image comprises a plurality of images representing the ROI, and
wherein in the generating of the at least one second image, brightnesses of the plurality of images are adjusted so that the brightnesses of the plurality of images are different from one another based on the first external signal.

5. The method of claim 1, wherein the previously generated images are previously generated ultrasound images.

6. A non-transitory computer-readable recording medium having recorded thereon a program for executing:
generating at least one first image representing a region of interest (ROI) by using echo signals corresponding to ultrasound waves irradiated toward the ROI;
displaying, on a screen, the at least one first image and a plurality of objects representing preset data of previously generated images, each of the plurality of objects showing a shape of a tissue in the ROI, wherein the plurality of objects respectively showing gradations of the ROI are displayed as image data that allows a degree of change in brightness of the gradations of the ROI to be recognized, and wherein the preset data includes a plurality of gradation data corresponding to the gradations of the previously generated images;
adjusting brightness of the at least one first image to generate at least one second image based on a first external signal for selecting a first object from the plurality of objects; and
displaying, on the screen, the at least one second image, wherein the gradations represented in the previously generated images vary from one image to another, wherein each of the plurality of objects includes icons for adjusting brightnesses of a plurality of regions in the at least one first image, and
wherein a number of the icons is the same as a number of the plurality of regions included in the at least one first image, and the brightnesses of the plurality of regions corresponding to the icons are adjusted.

7. The non-transitory computer-readable recording medium of claim 6, wherein the previously generated images are previously generated ultrasound images.

8. An apparatus for adjusting brightness of an ultrasound image, the apparatus comprising:
a memory configured to store preset data including a plurality of gradation data corresponding to gradations of previously generated images; and
a processor configured to:
generate at least one first image representing a region of interest (ROI) by using echo signals corresponding to ultrasound waves irradiated toward the ROI;
cause a screen to display the at least one first image and a plurality of objects representing the preset data, each of the plurality of objects showing a shape of a tissue in the ROI, wherein the plurality of objects respectively showing gradations of the ROI are displayed as image data that allows a degree of change in brightness of the gradations of the ROI to be recognized;

adjust brightness of the at least one first image to generate at least one second image based on a first external signal for selecting a first object from the plurality of objects; and cause the screen to display the at least one second image, wherein the gradations represented in the previously generated images vary from one image to another, wherein each of the plurality of objects includes icons for adjusting brightnesses of a plurality of regions in the at least one first image, and wherein a number of the icons is the same as a number of the plurality of regions included in the at least one first image, and the brightnesses of the plurality of regions corresponding to the icons are adjusted.

9. The apparatus of claim 8, wherein the previously generated images are previously generated ultrasound images.

* * * * *